(12) United States Patent
Barkhoudarian et al.

(10) Patent No.: US 7,061,607 B2
(45) Date of Patent: Jun. 13, 2006

(54) ENGINE SPECTROMETER PROBE AND METHOD OF USE

(75) Inventors: Sarkis Barkhoudarian, West Hills, CA (US); Scott A. Kittinger, Westlake, CA (US)

(73) Assignee: United Technologies Corporation, Hartford, CT (US)

( * ) Notice: Subject to any disclaimer, the term of this patent is extended or adjusted under 35 U.S.C. 154(b) by 345 days.

(21) Appl. No.: 10/428,693

(22) Filed: May 2, 2003

(65) Prior Publication Data

US 2004/0218175 A1 Nov. 4, 2004

(51) Int. Cl.
*G01J 3/30* (2006.01)
*G01J 3/28* (2006.01)

(52) U.S. Cl. ..................... 356/311; 356/326
(58) Field of Classification Search ............... 356/326, 356/311–315; 60/204, 240, 223, 200.1; 250/227.14
See application file for complete search history.

(56) References Cited

U.S. PATENT DOCUMENTS

| | | | | | |
|---|---|---|---|---|---|
| 4,558,951 A | * | 12/1985 | Ludman et al. | .............. | 356/451 |
| 5,748,090 A | * | 5/1998 | Borg et al. | ................. | 340/578 |
| 5,961,314 A | * | 10/1999 | Myhre et al. | ................. | 431/79 |
| 6,530,213 B1 | * | 3/2003 | Beck et al. | ................... | 60/204 |

* cited by examiner

*Primary Examiner*—Layla G. Lauchman
(74) *Attorney, Agent, or Firm*—Harness Dickey & Pierce P.L.C.

(57) ABSTRACT

The engine spectrometer probe and method of using the same of the present invention provides a simple engine spectrometer probe which is both lightweight and rugged, allowing an exhaust plume monitoring system to be attached to a vehicle, such as the space shuttle. The engine spectrometer probe can be mounted to limit exposure to the heat and debris of the exhaust plume. The spectrometer probe 50 comprises a housing 52 having an aperture 55 and a fiber optic cable 60 having a fiber optic tip 65. The fiber optic tip 65 has an acceptance angle 87 and is coupled to the aperture 55 so that the acceptance angle 87 intersects the exhaust plume 30. The spectrometer probe can generate a spectrum signal from light in the acceptance angle 506 and the spectrum signal can be provided to a spectrometer 508.

42 Claims, 5 Drawing Sheets

ENGINE SPECTROMETER PROBE AND METHOD OF USE

STATEMENT OF GOVERNMENT RIGHTS

The invention described herein was made in the performance of work under NASA Contract No. NAS8-01140 and is subject to the provisions of Section 305 of the National Aeronautics and Space Act of 1958 (72 Stat. 435, 42 U.S.C. 2457.) The U.S. Government has certain rights in this invention.

FIELD OF THE INVENTION

The present invention relates to analytical instrumentation, particularly, to an engine spectrometer probe and method of using the same.

BACKGROUND OF THE INVENTION

Rocket engines, jet engines, and gas turbines are subject to operational and environmental conditions that can cause material degradation and eventual component failure. Engine health must be monitored during operation, and inspection and preventative maintenance carried out during shut down. It is also desirable to monitor combustion during operation to assure that the combustion process occurs efficiently and as expected.

For rocket engines, such as the Space Shuttle Main Engines (SSME), borescopic inspections are performed after each flight or engine test. The borescope extends an optical probe into closed areas to provide visual inspection. Borescopic inspections are labor intensive and costly. Borescopic inspections are also intrusive, running they risk of introducing contamination into the engine and requiring engine requalification after inspection.

One method to provide real time, non-intrusive monitoring of engine health during operation is spectroscopic monitoring of the engine exhaust plume. Erosion, corrosion, and component failure can deposit engine material in the exhaust plume. Spectrometers can look for anomalous materials in the exhaust plume by monitoring the light spectrum from ultraviolet to infrared. By measuring the frequency and intensity of the light emitted from the exhaust plume, the spectrometer can determine the presence of anomalous materials or unexpected amounts of expected materials by comparison to standard and test measurements. This allows identification of those components which are wearing, corroding, or combusting, and assessment of the degree of wear, corrosion, or combustion. Spectroscopic monitoring in the ultraviolet range also provides an indication of the plume mixture and the combustion process, because the hydroxide radical has a characteristic emission in that range. The magnitude of the characteristic ultraviolet (UV) emission is related to the amount of hydroxide in the exhaust plume.

Optical spectrometers must be able to "see" the exhaust plume to provide an analysis. For hot-test engine firing in a test stand, a remote telescope is often used to feed the image of the exhaust plume to the optical spectrometer. The remote location can produce a poor image if atmospheric conditions are poor, with dust or precipitation in the air. Mounting of the telescopes to focus on a precise portion of the exhaust plume can be difficult. The difficulties are compounded for use of a remote telescope on an engine during flight, since the telescope must track a moving exhaust plume into space.

One approach has been to provide a spectrometer probe near the exhaust plume, attaching it to the engine or to the test stand. The spectrometer probes have been complex, due to optical, heat transfer, and materials problems. Previous designs required lenses and mirrors to direct the optical signal, particularly, high temperature sapphire lenses and a 90-degree reflecting mirror. Dichroic mirrors were required to reduce the infrared reflection on the receiving tip of the fiber optic cable within the probe. Exotic materials present problems in connecting the parts, such as brazing lenses in niobium lens holders, and welding the niobium lens holders to a Inconel® 718 nickel-chromium alloy probe housing to seal the spectrometer probe. Such connection of exotic materials requires development of new processes, which require expensive and difficult certification. The complexity of the spectrometer probe also resulted in a large cross-sectional housing area, about one half inch in diameter, which is exposed to a large heat flux. The complex spectrometer probes have been too expensive, too fragile and too heavy to fly on a vehicle.

Typical spectrometer probes have also focused on the mach diamond, which is the bright area in the engine exhaust plume caused by supersonic phenomena at atmospheric pressure. This presents a tracking problem because the mach diamond moves away from the engine and spreads out with decreasing atmospheric pressure. The mach diamond location also varies with other factors, such as the power level of the engine, the velocity of the emission gases, and the geometry of the nozzle. Tracking increases the chance of error and mechanism failure, and adds weight to the spectrometer probe. An additional tracking problem arises for vehicles with multiple engines: the mach diamonds overlap as they spread with decreasing atmospheric pressure, and each spectrometer probe sees multiple mach diamonds rather than a particular mach diamond.

Lack of a reliable spectrometer probe has prevented integrating exhaust plume monitoring into engine control systems. Although the exhaust plume contains information about engine heath that could be used to tune engine operation and avoid malfunctions by making decisions about adjusting fuel mixture, reducing engine power, isolating engine components, and shutting down the engine, no real time exhaust plume information has been available.

It is desirable, therefore, to provide an engine spectrometer probe and method of using the same that overcomes the above disadvantages.

SUMMARY OF THE INVENTION

The engine spectrometer probe and method of using the same of the present invention provides a simple engine spectrometer probe which is both lightweight and rugged, allowing an exhaust plume monitoring system to be attached to a vehicle, such as the space shuttle. The engine spectrometer probe can be mounted to limit exposure to the heat and debris of the exhaust plume.

In one preferred form the present invention provides real time engine health monitoring to avoid expensive, intrusive, labor-intensive post operation inspection.

The foregoing and other features and advantages of the invention will become further apparent from the following detailed description, read in conjunction with the accompanying drawings. The detailed description and drawings are merely illustrative of the invention rather than limiting, the scope of the invention being defined by the appended claims and equivalents thereof.

DETAILED DESCRIPTION OF THE PREFERRED EMBODIMENTS

Figure 1:
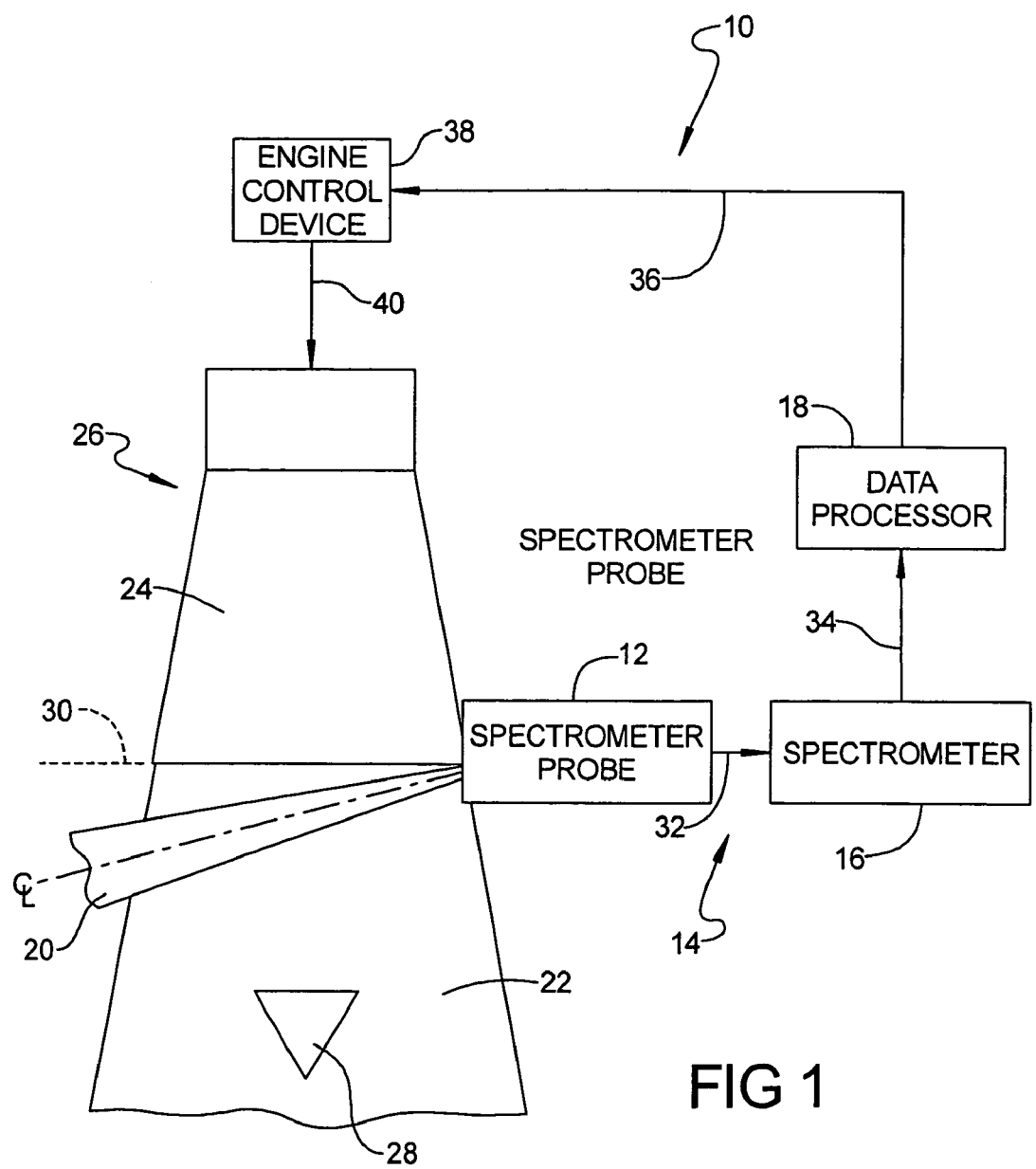
FIG. 1 shows a block diagram of a preferred embodiment an exhaust plume monitoring system using an engine spectrometer probe made in accordance with the present invention.

FIG. 1 shows a block diagram of a preferred embodiment of an exhaust plume monitoring system 10 using an engine spectrometer probe 12. The exhaust plume monitoring system 10 comprises the spectrometer probe 12, fiber optic cable 14, spectrometer 16, and data processor 18. The spectrometer probe 12 is optically coupled to and monitors the emitted light from a conical field of view 20 in an exhaust plume 22. The exhaust plume 22 is composed of reaction products exiting nozzle 24 of an engine 26. Mach diamond 28 may occur in the exhaust plume 22 for engines when the exhaust plume is in supersonic flow, but may be absent for other engine types. The spectrometer probe 12 can be attached to the nozzle 24 or can be attached to another part of the vehicle or a test stand (not shown). The data processor 18 can provide operational information to are engine control device 95 that controls the engine 26.

The engine 26 can be any combustion engine emitting high temperature exhaust to produce an exhaust plume 22. Such engines include, but are not limited to, rocket engines, jet engines, gas turbines, and diesel engines in vehicular or stationary applications. One example of a typical rocket engine is the Space Shuttle Main Engine (SSME). Engines generally use hydrogen or hydrocarbon-based fuels. The exhaust plume 22 emits a light from infrared to ultraviolet due to the combustive processes from operation of the engine 26. Light and the light spectrum as used herein includes the electromagnetic spectrum with the ultraviolet and infrared regions, not just visible light.

The spectrometer probe 12 is mounted so that the field of view 20 intersects the exhaust plume 22 below exit plane 30. The spectrometer probe 12 generates a spectrum signal 32 in response to the light of the exhaust plume 22. The spectrum signal 32 is provided to the spectrometer 16. The exit plane 30 is generally characterized and formed by the plane traversing the aft end of the engine 26 and typically includes the planar region circumscribed by the exhaust exit portion of the engine nozzle 24. Generally, the spectrometer probe 12 is mounted to maintain a view of the exhaust plume 22 and to be outside of the exhaust plume 22. It is desirable to keep the field of view 20 free from obstructions, such as bracing, instrumentation, or supports, that can interfere with the light from the exhaust plume 22. However, some obstruction is allowable without affecting results. A plurality of spectrometer probes can be used for redundancy and to assure a clear view of the whole exhaust plume. In one embodiment, the plurality of spectrometer probes can be used to triangulate any anomalies indicated and identify the problem location. In another embodiment, the plurality of spectrometer probes can be used for tomography analysis to provide sectional images of an exhaust plume. Both triangulation and tomography generate three dimensional plume data.

In one embodiment, the spectrometer probe 12 can be attached to the vehicle or engine, such as by attachment outside the aft edge of the exhaust nozzle 24 at the exit plane 30. In another embodiment, the spectrometer probe 12 can be a part of and integral to the exhaust nozzle 24. Such mounting is suitable for actual flight or test operation. In another embodiment, the spectrometer probe 12 can be attached to an engine test stand. Such mounting is suitable for test operation. Those skilled in the art will appreciate that many methods of temporary and permanent attachment, such as bolts or rivets, can be used to attach the spectrometer probe 12 to the vehicle or engine test stand.

The spectrometer probe 12 can be attached to the vehicle for real-time monitoring or for monitoring for post flight data processing. For a commercial airplane with a jet engine, the spectrometer probe 12 can be attached to a trailing edge or underside of a wing. For space vehicles, the spectrometer probe 12 can be attached to the engine, the tail support surfaces, or the wing support surfaces. Alternately, the spectrometer probe 12 can be attached to the booster rockets to monitor adjacent engines or the booster rockets themselves. Multiple spectrometer probes can be used to assure exhaust plume coverage, to triangulate events within an exhaust plume, to provide tomographic sectional images of an exhaust plume, or to monitor multiple engines.

For some engines, the exhaust plume 22 contains the mach diamond 28 because of supersonic exhaust flow from the engine 26. The location of the mach diamond 28 is a function of the engine design, engine nozzle geometry, power level, velocity of combustion gasses, and atmospheric pressure. The location of the mach diamond 28 may shift during operation of the engine 26. In aerospace flights, the mach diamond 28 shifts away from the exit plane 30 during ascent and disappears in space as atmospheric pressure decreases. Generally, the spectrometer probe 12 is mounted so that the field of view 20 is forward of any mach diamond 28.

The fiber optic cable 14 operably couples the spectrometer probe 12 with the spectrometer 16. The tip of the fiber optic cable 14 receives the light spectrum from the field of view 20 in the exhaust plume 22. The fiber optic cable 14 can be made of fused silica, glass, plastic, or another fiber optical material able to withstand the heat and the exhaust environment. The material of fiber optic cable 14 has a refraction index that defines the acceptance angle of the tip to detect and transmit the light spectrum. For example, fused silica has an acceptance angle of approximately 25 degrees. The conical field of view 20 is generally defined by the acceptance angle and is typically aimed at the area below the exit plane 30. The fiber optic cable 14 can be tailored to suit the particular wavelengths of interest. For example, the fiber optic cable 14 can include dopants to adjust the refractive index profile, or can limit hydroxyl, ions or metal impurities. The fiber optic cable 14 can have insulation, ablative coating, cooling systems, or a combination thereof, to protect it from engine heat. The fiber optic cable 14 can be supported to ensure it remains intact and transmits the signal to the spectrometer 16 during engine operation.

The spectrometer 16 is operably coupled to fiber optic cable 14 to receive the spectrum signal 32 and generate a spectrometer signal 34. The spectrometer 16 measures and analyzes the light spectrum detected by the spectrometer probe 12. The spectrometer 16 can be a broadband, high-resolution, optical multichannel analyzer spectrometer covering the near-ultraviolet to near-infrared waveband, a narrowband radiometer monitoring discrete wavelengths for particular elements, or a combination thereof. The spectrometer 16 can perform qualitative and quantitative analysis of the elements in the exhaust plume 22. In one embodiment, the spectrometer 16 can also include the data processor 18.

The data processor 18 is operably coupled to the spectrometer 16 to receive the spectrometer signal 34. The data processor 18 can be a general or special purpose computer, including various input, output, and storage devices. The data processor 18 can include computer storage media such as RAM, ROM, EPROM, flash memory or other memory technology; CD-ROM, digital versatile discs (DVD) or other optical storage; magnetic cassettes, magnetic tape, magnetic disc storage or other magnetic storage devices; or any other medium that can be used to store desired information. The data processor 18 can perform functions including, but not limited to, recording and managing spectral data, performing analyses, comparing spectra from multiple samples or multiple probes, providing data plots, and other general purpose functions. The data processor 18 can provide alarm and control indication, or provide alarm and control signals to other systems. In one embodiment, the data processor 18 can generate an engine health signal 36.

In one embodiment, an engine control device 313 can be responsive to the engine health signal 38 from the data processor 18 and generate an engine control signal 40, which controls the engine 26. The engine control device 38 can control performance and operation of the engine 26, such as control of engine throttle, fuel flow, fuel mixture, consolidated control systems, and control data processors. For example, an engine could be shut down if the data processor 18 detects off-normal operation.

Those skilled in the art will appreciate that a variety of means are available to operably couple the various components of the exhaust plume monitoring system 10. The various components communicate with radio frequency transmitters or other wireless devices. Data can be transmitted from a space flight to the ground, analyzed, and control signals returned to the space vehicle. Data can also be stored on board or on the ground during a space flight and analyzed after the space flight.

Figure 2:
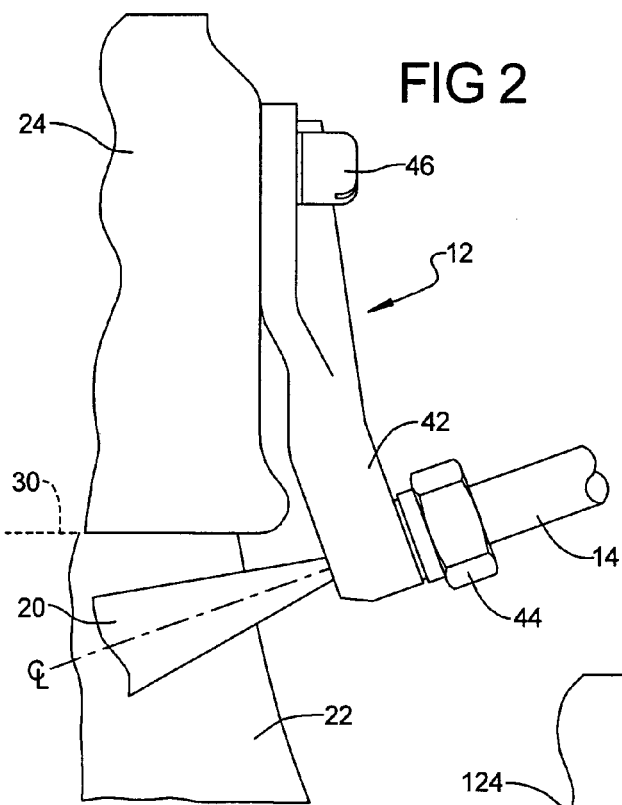
FIGS. 2–4 show side perspective, cross section, and front perspective views, respectively, of an engine spectrometer probe made in accordance with a preferred embodiment the present invention.
Figure 3:
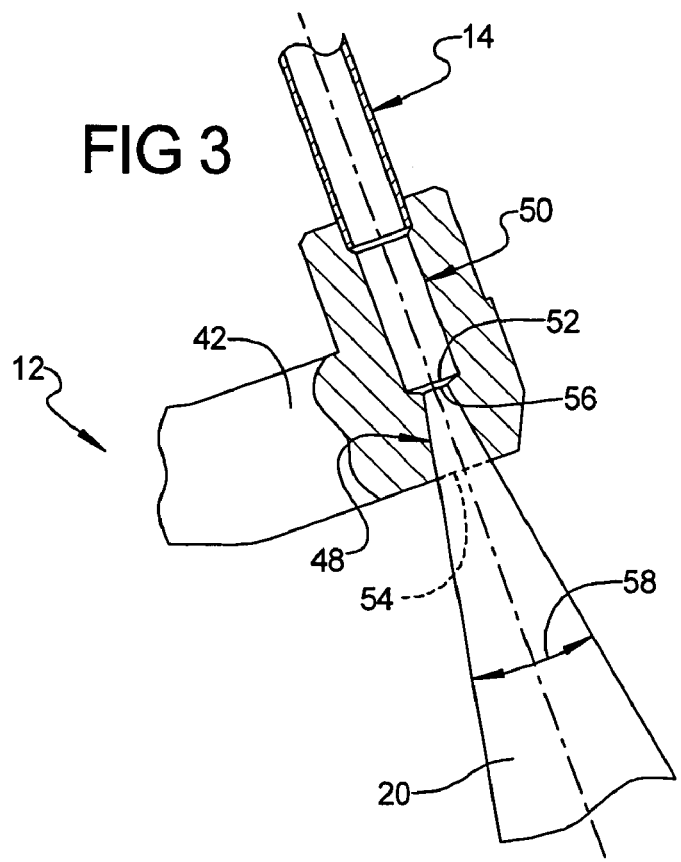
Figure 4:
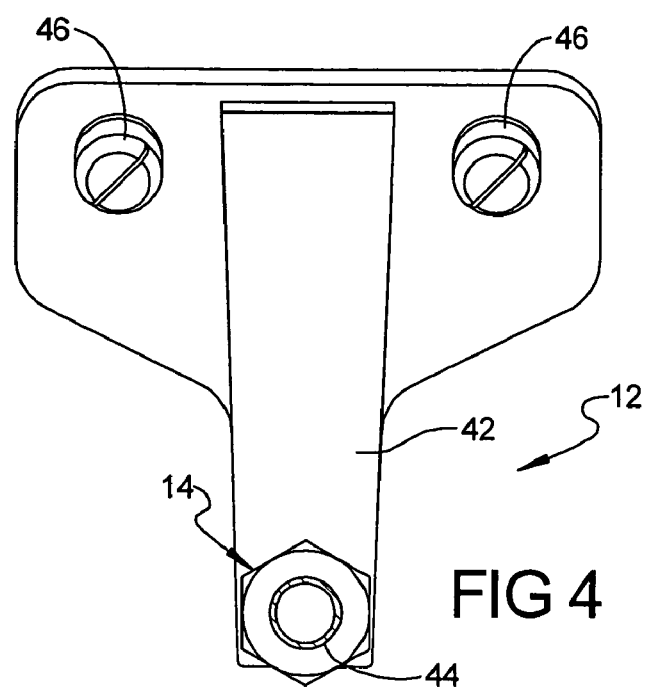

FIGS. 2–4, in which like elements share like reference numbers with each other and FIG. 1, show side perspective, cross section, and front perspective views, respectively, of an engine spectrometer probe made in accordance with the present invention.

Referring to FIG. 2, the spectrometer probe 12 comprises a housing 42 and the fiber optic tip of the fiber optic cable 14. The field of view 20 intersects the exhaust plume 22 to provide the spectrum signal to the fiber optic cable 14 in response to the light spectrum of the exhaust plume 22. The conical field of view 20 is generally defined by the acceptance angle of the fiber optic cable 14 and is typically aimed at the area below the exit plane 30. The major portion of the spectrometer probe 12 is shielded from the exhaust plume 22 behind the nozzle 24, avoiding the heat and turbulence. Insulation and cooling can be provided around the spectrometer probe 12 as long as the field of view 20 remains open. The housing 42 can be made of any material able to withstand high temperatures and harsh chemicals, and compatible with the materials to which the housing 42 is attached. In one embodiment, the housing 42 can be made of Inconel® 718 nickel-chromium alloy, which is the same material typically used for the nozzle 24. Those skilled in the art will appreciate that the housing 42 need not be separate from the nozzle 24, but can be integral to and fabricated as a part of the nozzle 24.

The fiber optic cable 14 can be attached to the spectrometer probe 12 with conventional means, such as threaded, bayonet, or crimped connectors. A connector 44 can be used to secure the fiber optic cable 14 to the housing 42. In one embodiment, the connector can be an SMA (Sub-Miniature A) connector.

Fasteners 46 can be used to attach the spectrometer probe 12 to the nozzle 24. The fasteners 46 can be conventional fasteners, such as bolts or rivets. To provide for high vibration operation as found for rocket engines, bolts can be secured with shims, washers, and self-locking nuts. Existing holes in the nozzle 24, such as the holes for the side load arrest mechanism bolts, can be used where possible.

FIG. 3 shows a cross section of a portion of the engine spectrometer probe 12. For clarity, the connector attaching the fiber optic cable 14 to the housing 42 is not shown in FIG. 3. The housing 42 has an aperture 48 in communication with a fiber optic receiver 50. The fiber optic cable 14 has a fiber optic tip 52. The housing 42 receives the fiber optic cable 14 in the fiber optic receiver 50, so that the fiber optic tip 52 is optically coupled to the aperture 48.

The aperture 48 has an outer opening 54 and an inner opening 56. The diameter of the inner opening 56 can be smaller than the diameter of the fiber optic receiver 50 and the fiber optic tip 52 to form a shoulder to limit the insertion depth of the fiber optic cable 14 in the fiber optic receiver 50. In one embodiment, the aperture 48 and the fiber optic receiver 50 can be fabricated in the nozzle 24.

The material of fiber optic cable 14 has a refraction index that defines the acceptance angle 58 of the fiber optic tip 52 to detect the light spectrum from the field of view 20. Light hitting the fiber optic tip 52 at angles outside of the acceptance angle 58 does not pass down the fiber optic cable 14. The acceptance angle 58 depends on the particular materials of the fiber optic cable 14, but generally is between 10 and 90 degrees. For example, fused silica has an acceptance angle of approximately 25 degrees. Fiber optic cable is widely available commercially, such as from Ocean Optics, Inc., of Dunedin, Fla., and Myriad Fiber Imaging Technology, Inc., of Dudley, Mass.

Those skilled in the art will appreciate that the aperture 48 can have any shape as long as the outer opening 54 and the inner opening 56 are collinear and have the desired diameters. In one embodiment, the aperture 48 can be conical. In other embodiments, the aperture 48 can be cylindrical, parabolic, spherical, or any other desired shape. Typically, the aperture 48 is conical with the diameters of the outer opening 54 and the inner opening 56 scaled so that the vertex angle of the cone is about equal to the acceptance angle of the fiber optic cable 14. The conical aperture 48 removes the least material from the housing 42 to maintain structural strength. In another embodiment, the outer opening 54 and the inner opening 56 can be scaled so that the angle of the aperture 48 is greater than the acceptance angle of the fiber optic cable 14, so the acceptance angle controls the signal to the fiber optic cable 14. In yet another embodiment, the outer opening 54 and the inner opening 56 can be scaled so that the angle of the aperture 48 is less than the acceptance angle of the fiber optic cable 14, so that the angle of the aperture 48 controls the signal to the fiber optic cable 14.

The length of the aperture 48 can be designed to protect the fiber optic tip 52 from debris and contaminants from the exhaust plume. In other embodiments, the length of the aperture 48 can be small, so that the outer opening 54 and the inner opening 56 are near each other and the fiber optic tip 52 is slightly recessed from the outside of the housing 42. The size and shape of the aperture 48 is generally selected to prevent light or debris entering the aperture 48 outside of the acceptance angle 58 from reaching the fiber optic tip 52 of the fiber optic cable 14: light or debris entering at a greater angle bounces off the wall of the housing 42 forming the aperture 48. Light striking the wall is scattered outside the acceptance angle 58 of the fiber optic tip 52. Debris striking the wall is scattered away from the fiber optic tip 52. Additional components can be disposed over or in the aperture 48 to protect the fiber optic tip 52 or to alter the light from the field of view 20. The additional components can include, but are not limited to, screens, gratings, optical gratings, lenses, prisms, mirrors, partial mirrors, transparent plates, diffusers, and combinations thereof.

FIG. 4 shows a front perspective view of the engine spectrometer probe 12. Those skilled in the art will appreciate that et number of shapes for the engine spectrometer probe 12 are possible. Typically, the shape can provide means for directing the fiber optic tip 52 of the fiber optic cable 14 in the specific direction of the exhaust plume and the capability of attaching the engine spectrometer probe 12 to a vehicle or a test stand. The shape can also minimize the amount of the engine spectrometer probe 12 exposed to the exhaust plume and be rugged enough to withstand anticipated vibration, shock, heat, and chemical exposure.

The housing 42 can have a compact shape to minimize weight, reduce vibration load, and provide strength. Compact is defined as being relatively short with mass distributed toward the center of the housing 42. Ideally, the housing 42 can be short, thin, skinny, and shallow. The housing 42 is designed to maintain a view of the exhaust plume 22, while avoiding excessive loading on the nozzle lip to which the fasteners 46 are attached and avoiding excessive loading on the fiber optic cable 14. The housing 42 can be made of the same material as the component to which it is attached. In one embodiment, the housing 42 can be made of Inconel® 718 nickel-chromium alloy, which is the same material typically used for the space shuttle engine nozzle.

The length between the fasteners 46 and the fiber optic cable 14 can be minimized to reduce vibration load on the engine nozzle. A shorter spectrometer probe produces lower vibration loading from the pendulum motion of the end of the housing 42 holding the fiber optic cable. Reducing the mass at the end of the housing 42 at the fiber optic cable 14 can also reduce vibration load on the engine nozzle. A spectrometer probe with mass toward the center also reduces vibration load on the engine nozzle. The transitions between shapes of the housing 42 can be eased to avoid stress concentrations and stress fractures. A compact spectrometer probe can be built with less material, making the spectrometer probe lighter and reducing vehicle fuel consumption. The offsetting design consideration is that the spectrometer probe must be long enough for the field of view to extend below the nozzle.

Figure 5:
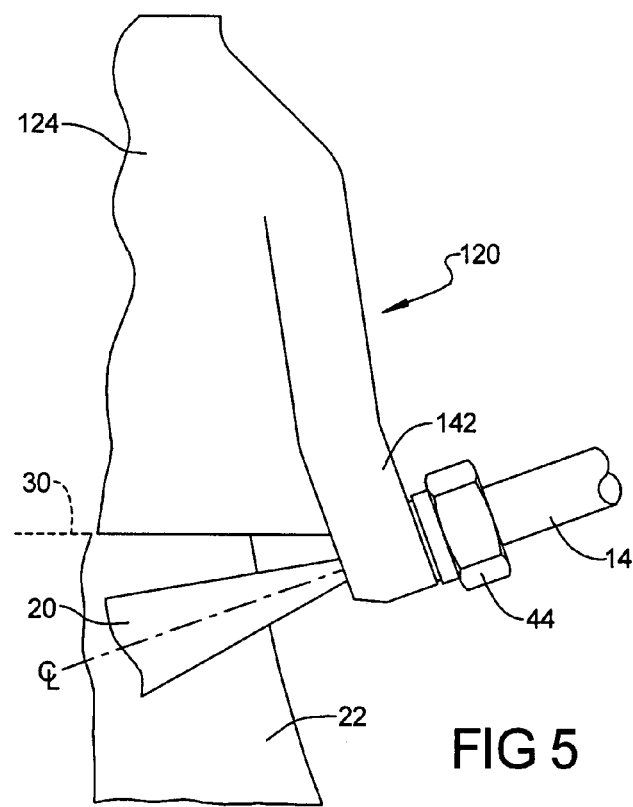
FIG. 5 shows another embodiment of an engine spectrometer probe made in accordance with the present invention.

FIG. 5, in which like elements share like reference numbers with FIGS. 2–4, shows another embodiment of an engine spectrometer probe 120 made in accordance with the present invention. The housing 142 of the spectrometer probe 120 is integral to a nozzle 124. The aperture and the fiber optic receiver (not shown) can be machined within the housing 142. An integral housing assures material compatibility between the housing and the nozzle, avoids the use of fasteners, and reduces areas of stress concentration.

Figure 6:
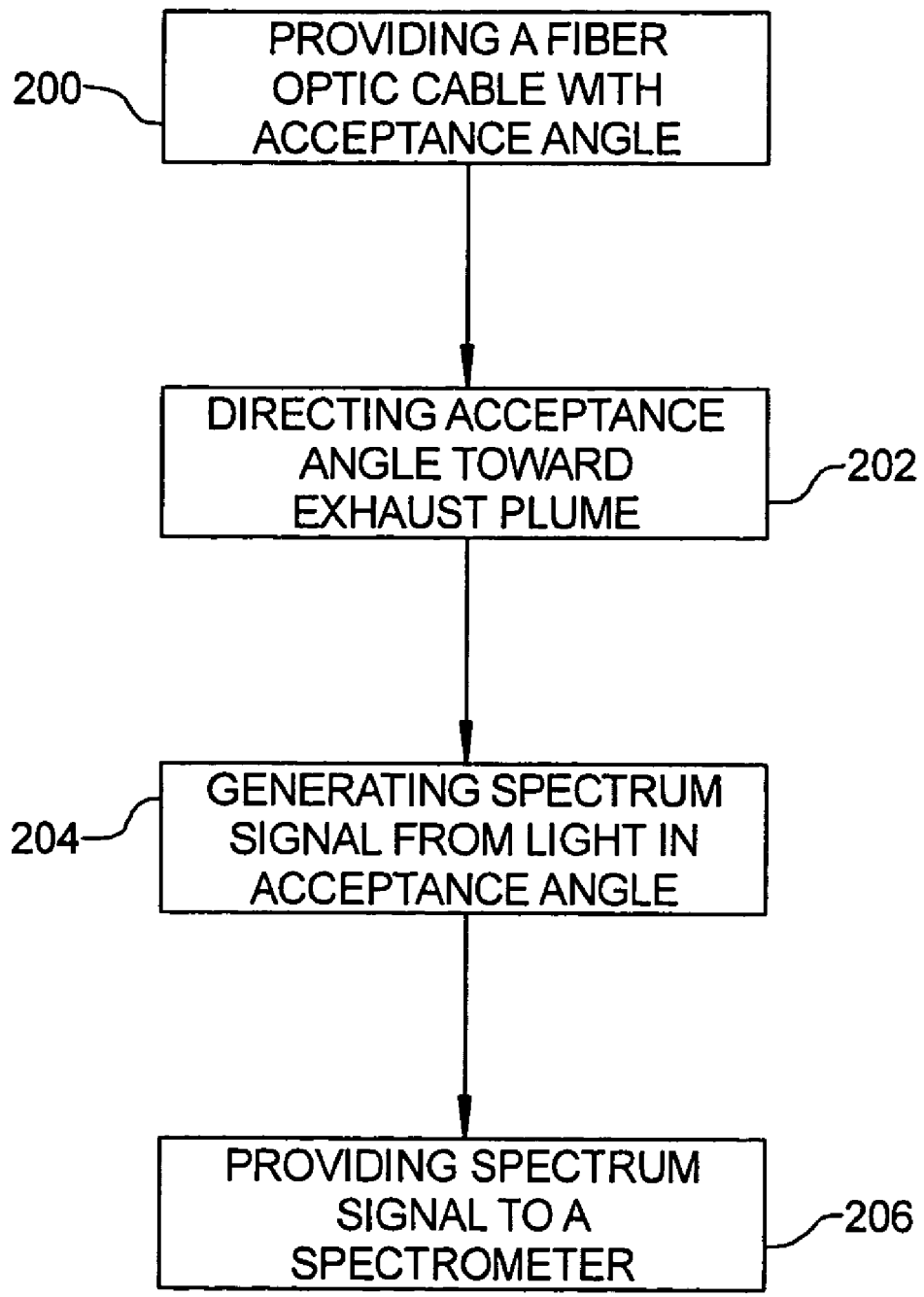
FIG. 6 shows a flow chart of a preferred method of using an engine spectrometer probe made in accordance with the present invention.

FIG. 6 shows a flow chart of a method of using an engine spectrometer probe to monitor an exhaust plume. At 200, a fiber optic cable is provided, the fiber optic cable having an acceptance angle. The acceptance angle is directed toward the exhaust plume at 202 and a spectrum signal is generated from light in the acceptance angle at 204. The spectrum signal is provided to a spectrometer at 206.

In one alternative implementation, the method can include the operations illustrated in FIG. 6, plus the operations of generating a spectrometer signal in response to the spectrum signal and providing the spectrometer signal to a data processor. The data processor can store or analyze the spectrometer signal. In analyzing the spectrometer signal, the data processor can compare the spectrometer signal to baseline data to produce analysis results. The baseline data can be data from the current engine run, historical data from prior engine runs, or library data for expected or off-normal engine operation for the engine type. The baseline data can include material fractions of expected materials indicating engine efficiency or limits on amounts of unexpected materials indicating erosion or component failure.

Library data for off-normal engine operation can be obtained by performing engine testing at controlled off-normal conditions. For example, if the data is to be used to detect unexpected elements in the exhaust plume 30 that would indicate component erosion, the particular element can be injected during an engine test run and the data saved as library data. Library data can include data for elements found in engine component materials, fuel, lubrication, cooling, or testing. Sacrificial elements not normally found in the engine 26 can be placed on or in engine components and their spectral signatures included in the library data. Monitoring the exhaust plume 30 for the sacrificial elements can provide an indication of component wear or failure.

Figure 7:
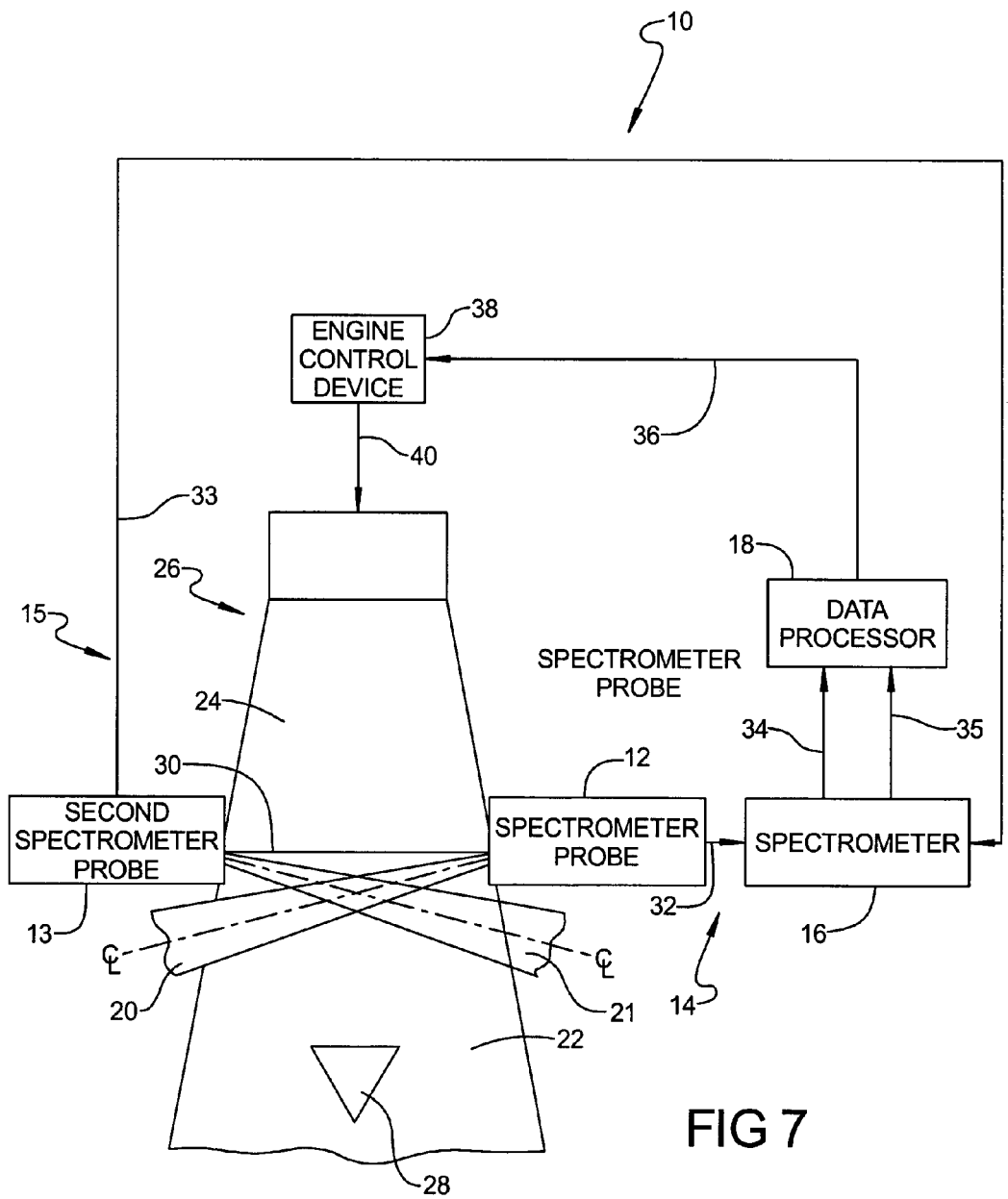
FIG. 7 shows a block diagram of a second embodiment of an exhaust plume monitoring system using an engine spectrometer probe made in accordance with the present invention.

The analysis results from comparing the spectrometer signal 34 to baseline data can be used for control and indication. The analysis can include quantitative as well as qualitative review. Uses include operational control, fault detection, fault isolation, safety and reliability decision-making, maintenance decision-making, maintenance scheduling, fault prediction, and environmental compliance. Automatic control can adjust engine operation through an engine health signal to an engine control device. The operator can use the analysis results to make decisions regarding engine operation and safety. The operator can monitor the fuel mixture ratio determined from ultraviolet emissions due to hydroxyl radicals and the fuel mixture ratio. Maintenance can use the analysis results to provide overhaul and preventive maintenance if undesirable trends are detected. Triangulation and tomography can provide three dimensional plume data as an indication of specific components requiring attention. The three dimensional plume data can include information about the plume, such as emission material concentration or ultraviolet emissions, as a function of position within the plume. Triangulation can be used to pinpoint a location of specific activity and tomography can be used to produce planar sectional images. The analysis results can also be used to determine appropriate maintenance intervals. The analysis results can be used for jet engines to monitor compliance with emission regulations for concentrations of chemicals, such as oxides of nitrogen, oxides of carbon, hydrocarbons, and carbon monoxide. Triangulation and tomography may require the use of multiple spectrometer probes, as shown in FIG. 7, in order to collect three-dimensional plume data. Second spectrometer probe 13 is shown with a second spectrometer field of view 21 which overlaps field of view 20 of spectrometer probe 12. Second spectrometer probe 13 may generally be placed anywhere around the periphery of nozzle 24 as may be convenient for collecting three-dimensional plume data. Second spectrometer probe 13 sends a second spectrum signal 33 along second fiber optic cable 15 to spectrometer 16, which may generate a second spectrometer signal 35 in addition to spectrometer signal 34. Both spectrometer signal 34 and second spectrometer signal 35 may be analyzed by data processor 18 and/or engine control device 38 using triangulation or tomography to determine the presence and location of predetermined elements in the exhaust plume 22.

In another implementation, the method can include the operations illustrated in FIG. 6, plus generating a spectrometer signal in response to the spectrum signal, providing the spectrometer signal to a data processor, generating an engine health signal in response to the spectrometer signal, providing the engine health signal to an engine control device, the engine control device generating an engine control signal in response to the engine health signal, and providing the engine control signal to the engine.

The engine health signal can be one of a number of engine status signals supplied to the engine control device 95 that are used to determine engine 26 operation. The various engine status signals can be used individually or in combination. For example, the engine control device 95 can be responsive to an engine health signal and an engine vibration signal, so that unexpected plume activity combined with unusual vibration would trigger corrective action.

The engine 26 can be responsive to the engine control signal 40 to adjust operating parameters or take safety measures. As an example of operational adjustment, the fuel mixture ratio can be determined from ultraviolet emissions due to hydroxyl radicals and the fuel mixture ratio adjusted to maintain optimal operation. One example of a safety measure is shutting down or reducing engine power on detecting an off-normal concentration of a particular element indicating erosion or component failure. Another example is isolating engine systems or components if material concentration or location indicates failure of a particular engine system or component. Yet another example is reducing engine power or shutting down the engine if metal is detected in the exhaust plume 22.

For jet engines or other engines subject to emission limits, the engine health signal can include measured emission data for predetermined chemicals, such as oxides of nitrogen, oxides of carbon, hydrocarbons, and carbon monoxide. The engine control device can adjust the engine control signal in response to the measured emission data, so that the engine operates in response to the engine control signal to maintain the measured emission data within predetermined emission limits.

It is important to note that FIGS. 1–6 illustrate specific applications and embodiments of the present invention, and is not intended to limit the scope of the present disclosure or claims to that which is presented therein. Upon reading the specification and reviewing the drawings hereof, it will become immediately obvious to those skilled in the art that myriad other embodiments of the present invention are possible, and that such embodiments are contemplated and fall within the scope of the presently claimed invention.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

We claim:

1. A spectrometer probe for detecting possible damage occurring to an engine generating an exhaust plume, the spectrometer probe comprising:
    a housing, the housing having an aperture; and
    an optical transmitting component, the optical transmitting component having a tip, the tip having an acceptance angle;
    wherein the tip is disposed adjacent the aperture so that the acceptance angle intersects the exhaust plume and collects a signal for spectral analysis to detect the presence of a material in the exhaust plume relating to a component of the engine, to thus indicate possible damage occurring to the engine.

2. The spectrometer probe of claim 1, wherein the aperture is conical.

3. The spectrometer probe of claim 2, wherein the aperture has a vertex angle and the acceptance angle is about equal to the vertex angle of the aperture.

4. The spectrometer probe of claim 1, wherein the acceptance angle is between 10 and 90 degrees.

5. The spectrometer probe of claim 1, wherein the acceptance angle is about 25 degrees.

6. The spectrometer probe of claim 1, wherein the shape of the aperture is selected from the group consisting of conical, cylindrical, parabolic, and spherical.

7. The spectrometer probe of claim 1, wherein the housing has a wall about the aperture, and light striking the wall is scattered outside the acceptance angle of the tip of the optical transmitting component.

8. The spectrometer probe of claim 1, wherein the housing has a wall about the aperture, and debris striking the wall is scattered away from the tip of the optical transmitting component.

9. The spectrometer probe of claim 1, wherein the optical transmitting component comprises a fiber optic cable made of a material selected from the group consisting of fused silica, glass, and plastic.

10. The spectrometer probe of claim 1, wherein additional components are disposed in the aperture, the additional components being selected from the group consisting of screens, gratings, optical gratings, lenses, prisms, mirrors, partial mirrors, transparent plates, diffusers, and combinations thereof.

11. The spectrometer probe of claim 1, wherein the housing is compact.

12. The spectrometer probe of claim 1, wherein the engine has a nozzle and the housing is integral to the nozzle.

13. An exhaust plume monitoring system for detecting possible damage occurring to an engine generating an exhaust plume, the system comprising:
    a fiber optic cable, the a fiber optic cable having an acceptance angle;
    a housing, the housing supporting a portion of the fiber optic cable and directing the acceptance angle toward the exhaust plume; and
    a spectrometer, the spectrometer operably coupled to the fiber optic cable to receive a signal for spectral analysis to detect the presence of a material in the exhaust plume relating to a component of the engine, to thus indicate possible damage occurring to the engine.

14. The exhaust plume monitoring system of claim 13, further comprising a data processor, the data processor being operably coupled to the spectrometer.

15. The exhaust plume monitoring system of claim 14, further comprising an engine control device, the engine control device being operably coupled to the data processor.

16. The exhaust plume monitoring system of claim 13, wherein the housing includes an aperture, the acceptance angle being disposed within the aperture.

17. The exhaust plume monitoring system of claim 13, further comprising:
a second fiber optic cable, the second fiber optic cable having second acceptance angle; and
a second housing, the second housing directing the second acceptance angle toward the exhaust plume;
wherein the spectrometer is operably coupled to the second fiber optic cable to receive a second signal for spectral analysis to detect the presence of a material in the exhaust plume relating to a component of the engine, to thus indicate possible damage occurring to the engine.

18. A method of monitoring an exhaust plume of an engine to detect possible damage occurring to the engine comprising:
directing an optical transmitting element having an acceptance angle toward the exhaust plume;
generating a spectrum signal from light in the acceptance angle; and
providing the spectrum signal through the optical transmitting element to a spectrometer to detect the presence of a material in the exhaust plume relating to a component of the engine, to thus indicate possible damage occurring to the engine.

19. The method of claim 18, further comprising generating a spectrometer signal in response to the spectrum signal and providing the spectrometer signal to a data processor.

20. The method of claim 19, further comprising storing the spectrometer signal.

21. The method of claim 19, further comprising analyzing the spectrometer signal.

22. The method of claim 21, wherein analyzing the spectrometer signal comprises comparing the spectrometer signal to baseline data.

23. The method of claim 22, wherein the baseline data is for a current engine run.

24. The method of claim 22, wherein the baseline data is from a data library.

25. The method of claim 24, wherein the data library is selected from the group consisting of off-normal data from injection testing and sacrificial element data.

26. The method of claim 21, wherein analyzing the spectrometer signal comprises analyzing the spectrometer signal to determine the fuel mixture.

27. The method of claim 19, further comprising:
generating an engine health signal in response to the spectrometer signal;
providing the engine health signal to an engine control device, the engine control device generating an engine control signal in response to the engine health signal; and
providing the engine control signal to the engine.

28. The method of claim 27, wherein the engine is responsive to the engine control signal to take action selected from the group consisting of adjusting fuel mixture, reducing engine power, isolating engine components, and shutting down the engine.

29. The method of claim 27, wherein the engine is responsive to the engine control signal to take action in real time.

30. The method of claim 27, wherein the engine is responsive to a plurality of engine status signals.

31. The method of claim 27, further comprising:
including measured hydroxyl radical emission data in the engine health signal;
adjusting the engine control signal in response to the measured hydroxyl radical emission data; and
adjusting fuel mixture in response to the engine control signal.

32. The method of claim 27, further comprising:
including measured metal emission data in the engine health signal;
adjusting the engine control signal in response to the measured metal emission data; and
taking action in response to the engine control signal, the action selected from the group consisting of reducing engine power and shutting down the engine.

33. The method of claim 27, further comprising:
including measured emission data in the engine health signal; adjusting the engine control signal in response to the measured emission data; and
operating the engine in response to the engine control signal to maintain the measured emission data within predetermined emission limits.

34. The method of claim 33, wherein the measured emission data is for chemicals selected from the group consisting of oxides of nitrogen, oxides of carbon, hydrocarbons, and carbon monoxide.

35. The method of claim 19, further comprising:
using a second optical transmitting element having a second acceptance angle and directing the second acceptance angle toward the exhaust plume;
generating a second spectrum signal from light in the second acceptance angle;
generating a second spectrometer signal in response to the second spectrum signal; and
providing the second spectrometer signal to the data processor to detect the presence of a material in the exhaust plume relating to a component of the engine, to thus indicate possible damage occurring to the engine.

36. The method of claim 35, further comprising analyzing the spectrometer signal and the second spectrometer signal to generate three dimensional plume data.

37. The method of claim 35, further comprising analyzing the spectrometer signal and the second spectrometer signal by a method selected from the group consisting of triangulation and tomography.

38. A system for monitoring an exhaust plume of an engine comprising:
means for transmitting an optical signal for spectral analysis to detect the presence of at least one predetermined element in the exhaust plume, the optical signal transmitting means having an acceptance angle; and
means for directing the acceptance angle toward the exhaust plume.

39. The system of claim 38, wherein light in the acceptance angle generates a spectrum signal and further comprising means for providing the spectrum signal to a means for measuring the spectrum signal.

40. The system of claim 39, wherein the spectrum signal measuring means generates a spectrometer signal and further comprising means for processing the spectrometer signal.

41. The system of claim 40, wherein the spectrometer signal processing means generates an engine health signal and further comprising means for controlling the engine responsive to the engine health signal.

42. A spectrometer probe fore detecting possible damage occurring to an engine generating an exhaust plume, the spectrometer probe comprising:

a housing, the housing having an aperture; and an optical transmission medium have a tip portion, the tip portion imaging a selected area within the housing through the aperture, the exhaust plume flowing through the selected area; and wherein the optical transmission medium collects a signal for spectral analysis to detect the presence of a material in the exhaust plume relating to a component of the engine, to thus indicate possible damage occurring to the engine.

\* \* \* \* \*